(12) United States Patent
Knop et al.

(10) Patent No.: US 9,771,822 B2
(45) Date of Patent: Sep. 26, 2017

(54) CARBON-DIOXIDE-NEUTRAL COMPENSATION FOR CURRENT LEVEL FLUCTUATIONS IN AN ELECTRICAL POWER SUPPLY SYSTEM

(75) Inventors: Klaus Knop, Sulzburg (DE); Lars Zoellner, Cologne (DE)

(73) Assignee: Carbon-Clean Technologies AG, Cologne (DE)

( * ) Notice: Subject to any disclaimer, the term of this patent is extended or adjusted under 35 U.S.C. 154(b) by 0 days.

(21) Appl. No.: 13/819,174

(22) PCT Filed: Sep. 2, 2011

(86) PCT No.: PCT/EP2011/004426
§ 371 (c)(1),
(2), (4) Date: May 9, 2013

(87) PCT Pub. No.: WO2012/028326
PCT Pub. Date: Mar. 8, 2012

(65) Prior Publication Data
US 2013/0214542 A1    Aug. 22, 2013

(30) Foreign Application Priority Data

Sep. 3, 2010 (EP) .................................... 10009165
Sep. 20, 2010 (EP) .................................... 10009893

(51) Int. Cl.
*C25B 1/04* (2006.01)
*F01D 15/10* (2006.01)
(Continued)

(52) U.S. Cl.
CPC ................ *F01D 15/10* (2013.01); *C07C 1/12* (2013.01); *C07C 29/1518* (2013.01); *C25B 1/04* (2013.01);
(Continued)

(58) Field of Classification Search
CPC .................................................... C07C 1/0485
(Continued)

(56) References Cited

U.S. PATENT DOCUMENTS 4,189,925 A * 2/1980 Long .............................. 60/652
4,665,688 A * 5/1987 Schiffers et al. ............... 60/784
(Continued)

FOREIGN PATENT DOCUMENTS

CA    2747097 A1 *  6/2010
DE    43 32 789 A1    3/1995
(Continued)

*Primary Examiner* — Brian W Cohen
(74) *Attorney, Agent, or Firm* — David S. Safran

(57) ABSTRACT

A method is provided for carbon-dioxide-neutral compensation for current level fluctuations in an electrical power supply system as a result of peaks and troughs in the generation of electrical energy. When a generation peak occurs, electrical energy produced from a regenerative energy source is used in an electrolysis unit for hydrogen generation. A hydrogen flow generated in the electrolysis unit is supplied to a reactor unit that catalytically generates an energy-carrier flow containing hydrocarbon. In a generation trough, the produced energy-carrier flow is burned in a combustion chamber. The thermal energy of the flue-gas flow formed by the combustion is used to generate electrical energy in a turbine process. The generated electrical energy is fed into the electrical power supply system. The flue-gas flow is supplied to the reactor unit as a carbon source for generation of the energy-carrier flow.

15 Claims, 1 Drawing Sheet

(51) Int. Cl.
  *C07C 1/12* (2006.01)
  *C07C 29/151* (2006.01)
  *C25B 1/12* (2006.01)
  *C25B 15/00* (2006.01)

(52) U.S. Cl.
  CPC .............. *C25B 1/12* (2013.01); *C25B 15/00*
    (2013.01); *Y02E 50/18* (2013.01); *Y02E*
    *60/366* (2013.01); *Y02E 70/10* (2013.01);
    *Y02P 20/133* (2015.11)

(58) Field of Classification Search
  USPC ................................ 205/628–639, 335, 337
  See application file for complete search history.

(56) References Cited

U.S. PATENT DOCUMENTS

| | | | |
|---|---|---|---|
| 5,342,702 A * | 8/1994 | MacGregor | 205/637 |
| 6,997,965 B2 * | 2/2006 | Katayama | 48/202 |
| 7,989,507 B2 | 8/2011 | Rising | |
| 2002/0025457 A1 * | 2/2002 | Dodd et al. | 429/9 |
| 2004/0171701 A1 * | 9/2004 | Shaw | 518/700 |
| 2009/0308738 A1 * | 12/2009 | Richards et al. | 204/252 |

FOREIGN PATENT DOCUMENTS

| | | |
|---|---|---|
| DE | 10 2006 034 712 A1 | 1/2008 |
| WO | 2009/016228 A1 | 2/2009 |
| WO | 2010/069385 A1 | 6/2010 |
| WO | 2010/069622 A1 | 6/2010 |
| WO | 2010/069685 A1 | 6/2010 |

\* cited by examiner

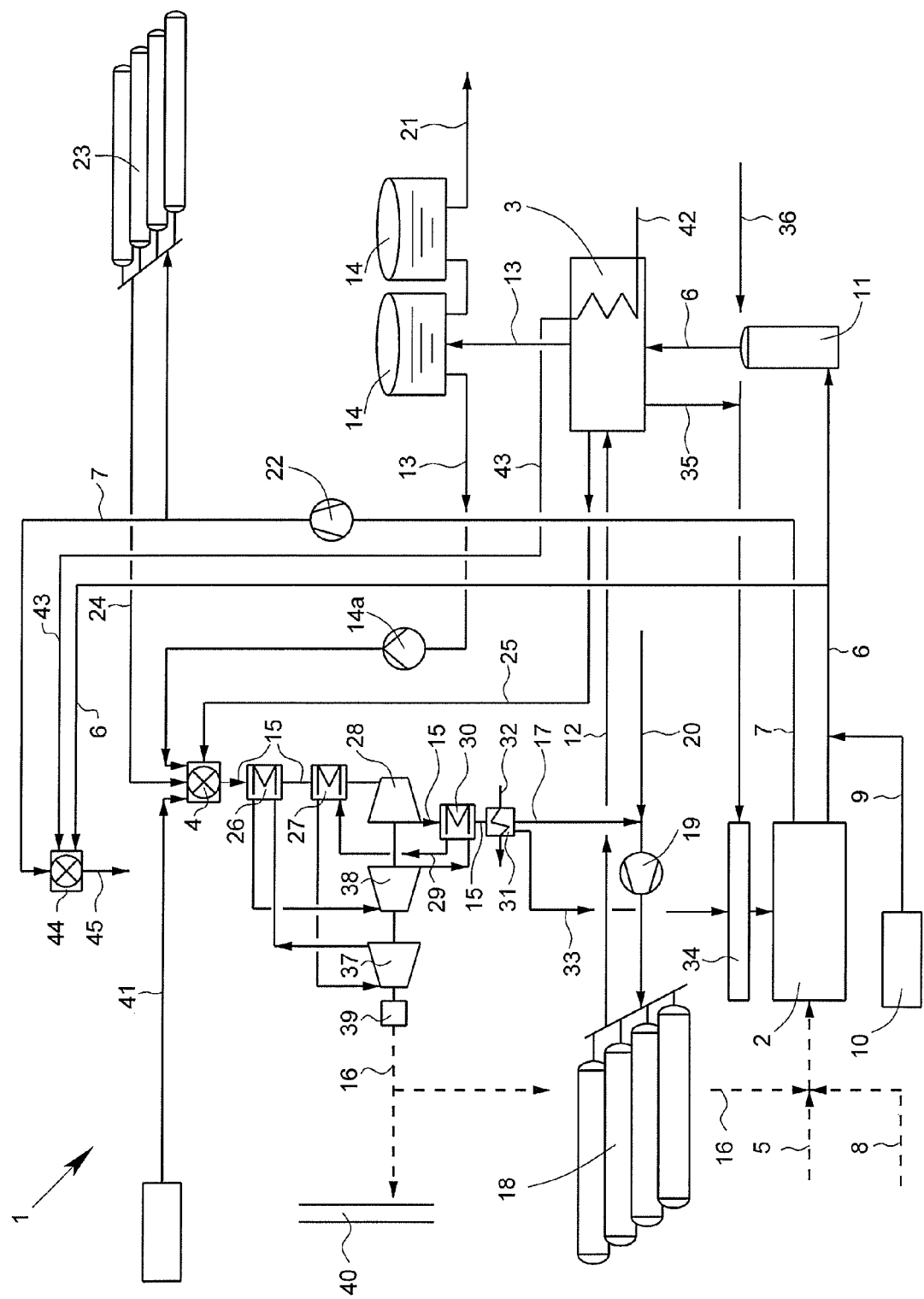

CARBON-DIOXIDE-NEUTRAL COMPENSATION FOR CURRENT LEVEL FLUCTUATIONS IN AN ELECTRICAL POWER SUPPLY SYSTEM

BACKGROUND OF THE INVENTION

Field of the Invention

The invention relates to a method and an energy-carrier production installation for carbon-dioxide-neutral compensation of current level fluctuations in a power supply system as a result of generation peaks and generation troughs in the generation of electrical energy, in particular from regenerative energy sources. In particular, the invention relates to the generation of electrical energy by conversion of wind energy, solar energy, geothermal heat, by utilizing biomass, and/or tidal forces.

Description of Related Art

Considering the increasing scarcity of fossil fuels in the long term and the threat of global warming caused by green house gases, development and exploitation of renewable regenerative energy sources such as wind and solar energy, but also geothermal heat and tidal power as alternatives or parallel to conventional energy generation from fossil energy carriers becomes increasingly important.

One drawback in using regenerative energy sources for the generation of electrical energy is the fact that the natural supply situation is difficult to predict and is influenced by natural fluctuations. So for instance, depending on changes caused by the weather, time of the day or season, generation peaks or generation troughs of the electrical energy generated from regenerative energy sources occur. Fluctuating electricity generation in particular caused by instable weather conditions, times of the day or seasonal influences is faced by a non constant electricity demand from the consumer.

When electricity generated from regenerative energy sources is fed into an electrical power supply system, generation peaks and generation troughs can cause major problems. Adaptation of power plant technology to such fluctuating current levels involves considerable efforts.

For instance, there are uncertainties in the generation of electricity by using wind power, which are caused by unpredictable weather conditions, wherein in periods of wind calm conventional power plants are operated at peak load during peak demand hours while in periods, when sufficient wind is available for the generation of electricity, the demand for energy can be so low. As such, the power plant has to be operated below its capacity and, thus, causes higher carbon dioxide emissions. Moreover, when the operator of a wind power station is not able to feed the power into the power grid because of a potentially dangerous grid overload, the wind power plant has to be shut down, thus reducing the operating profitability of the same.

Thus, in the field of utilization of regenerative energy sources for the generation of electrical energy there is a need for a cost-effective and efficient method in order to be able to compensate generation peaks and generation troughs.

From prior art, a method is known for breaking down water into hydrogen and oxygen by means of electrolysis. But storing hydrogen is a complicated and costly process. Moreover, the transport of hydrogen to the place of its actual use requires a hydrogen infrastructure, which is usually not in place. Another disadvantage is the fact that oxygen released during electrolysis is used in limited ways only. Thus, prior art provides a method for conversion of carbon dioxide and hydrogen into an energy-carrier, which contains hydrocarbon, by using catalysts such as methanol and methane. Methods for providing storable and transportable carbon-based energy carriers by using carbon dioxide as carbon source and by using electrical energy are disclosed in International Patent Application Publication No. WO 2010/069622 A1. In addition, the catalytic production of methanol is also disclosed in International Patent Application Publication No. WO 2010/069385 A1 and in International Patent Application Publication No. WO 2010/069685 A1.

SUMMARY OF THE INVENTION

An objective of the present invention is to provide a method and an energy-carrier production installation of the above mentioned type, which allows the compensation of fluctuations of the current thus produced with a high profitability and efficiency, when the compensation is carbon-dioxide neutral, which means, that basically no carbon dioxide will be released.

The above objective is achieved by a method having the features disclosed herein and an energy-carrier production installation as disclosed herein.

The present invention is based on the idea of feeding electrical energy, which is not generated in a constant manner and/or in fluctuating amounts into an electrolysis unit, in order to produce hydrogen using the electrical energy, which has been fed into the unit and by subsequently converting the hydrogen in a reactor unit by especially catalytic conversion using carbon dioxide, into an energy-carrier containing hydrocarbon, the same being preferably methanol or methane. By subsequently burning the generated energy-carrier flow containing hydrocarbon partially and as required in a combustion chamber of the energy-carrier production installation, a hot flue-gas flow is released, which can be utilized for the generation of electricity by a downstream gas turbine process and/or steam turbine process. By feeding back the thus generated electricity into the power supply system, it is possible to compensate generation peaks and generation troughs occurring during the generation of electric power, in particular from regenerative energy sources, moreover, in particular when generating electric energy through wind power stations and/or photovoltaic systems, by providing a steady current output over long periods of time. The method according to the invention and the energy-carrier production installation according to the invention thus are particularly suitable for compensating fluctuations that occur when generating electricity in wind farms. Moreover, the method according to the invention reduces the need for back-up power plants, since electricity in form of the energy-carrier flow is stored temporarily.

By employing the method according to the invention and the energy-carrier production installation according to the invention it is possible, to provide larger or smaller quantities of electricity at short notice. For a carbon-dioxide-neutral compensation of generation peaks and generation troughs according to the invention it is provided for the flue-gas-flow, produced in the combustion chamber, to be supplied to the reactor unit as carbon source for the generation of the energy-carrier flow containing hydrocarbon. Thus, a closed carbon dioxide cycle is achieved, which reduces the carbon footprint by avoiding carbon dioxide emissions. Simultaneously, the invention provides for electrical energy storage in form of an energy-carrier flow containing hydrocarbon, which allows the stored energy-carrier containing hydrocarbon to be reused by a power plant process for the generation of electricity, at times of increased electricity demand and for the thus generated electricity to be fed into an electrical power supply system.

Part of the energy thus generated in a gas turbine process and/or steam turbine process of the installation according to the invention can be reserved for internal use by the energy-carrier production installation, such as the compaction/compression of material flows and/or for the electrolysis of water in order to produce the hydrogen flow in the electrolysis unit.

In principle, the reactor unit can also be provided a carbon dioxide flow from an external carbon dioxide source, that is, a carbon dioxide flow which has not been generated on-site by combustion in the combustion chamber of the energy-carrier production installation. In this manner it is possible to increase the yield during the generation of the energy-carrier containing hydrocarbon in the reactor unit, without having to burn the energy-carrier produced in the reactor unit on-site in order to be able to provide sufficient quantities of carbon dioxide for producing the energy-carrier in the reactor unit. Instead, the energy-carrier produced in this way can be sold as a product and used outside the energy-carrier production installation, for instance as petrol substitute and/or as raw material for the chemical industry. The part of the energy-carrier production installation according to the invention, which is used for the generation of electricity does not have to be in operation whereby the energy-carrier production installation is used exclusively for the production of the energy-carrier containing hydrocarbon. In this case, generation of power on-site is not proposed. In principle it is also possible to burn a part of the energy-carrier produced, in order to generate electricity on-site, while another part can be provided exclusively for external use.

In addition, the combustion chamber can be supplied at least one additional (external) energy-carrier flow containing hydrocarbon, in particular natural gas. In this manner it is also possible to supply carbon dioxide for the generation of the energy-carrier containing hydrocarbon in the reactor unit and to generate electric power through the gas turbine process and/or steam turbine process by utilizing the flue gas flow produced in the combustion chamber by burning the external energy-carrier flow in the combustion chamber. This is particularly advantageous when the energy-carrier production installation according to the invention is used exclusively for the production of the energy-carrier in the reactor unit, moreover, in particular, when the available electrical energy from a regenerative energy source is not sufficient for providing enough electrical energy to the electrolysis unit.

Furthermore, when electricity prices are low it possible to feed electricity from fossil energy sources into the electrolysis unit in order to generate a cost-effective energy-carrier containing hydrocarbon in the reactor unit, which can be used for the generation of electricity, after the electricity prices have gone up again. For instance, when over a short period of time wind- or solar energy is not available, it is possible to feed electricity which has been produced in a conventional manner from natural gas into the electrolysis unit, permitting a cost-effective and climate-neutral generation of the energy-carrier in the reactor unit free of carbon dioxide emissions, owing to the high level of efficiency of the energy-carrier production installation according to the invention. Thus, high economic viability of the method and the energy-carrier production installation according to the invention is ensured, wherein in principle also mixed currents from renewable and fossil energy can be used for the electrolysis. With respect to the electricity prices, the above described process or mode of operation of the energy-carrier production installation according to the invention is particularly advantageous, since the same are fluctuating according to time of the day and season (summer-winter-cycle; day-night-cycle).

Apart from that, the hydrogen flow produced by electrolysis can be combined with another hydrogen flow, for instance one produced by fermentation and/or gasification of biomass, in order to homogenize or increase the volumetric flow of the hydrogen fed into the reactor unit. Thus, for instance, it is possible to integrate the use of biomass for the generation of electricity from renewable sources in the plant concept of the energy-carrier production installation according to the invention. In order to ensure a high level of purity for a hydrogen flow, which is not generated by electrolysis, a gas purification system of a relevant design can be provided upstream. The additional hydrogen flow can also be supplied directly to the reactor unit.

By using oxygen instead of air it is possible to extract almost pure carbon dioxide as flue-gas flow, wherein according to the invention, it can be provided for an oxygen flow generated in an electrolysis unit to be supplied to the combustion chamber in order to burn the energy-carrier-flow.

For the generation of the hydrogen flow and oxygen flow, a pressure-electrolysis unit can be provided, with the pressure of the hydrogen and/or oxygen ranging from 10 to 200 bar, preferably from 30 to 100 bar, in particular at least from 60 to 80 bar. From prior art and to persons skilled in the art, suitable alkaline and polymer electrolyte membrane-pressure electrolysis methods are known, wherein in the future it will be possible to achieve a system pressure of more than 200 bar.

The compressed hydrogen can be supplied to a pressure accumulator functioning as buffer tank and stored in the same. The oxygen flow can be stored at a storage pressure of at least 30 bar, in particular approx. 60 bar or higher. Subsequently, an oxygen flow with a storage pressure of at least 30 bar, in particular approx. 60 bar or higher can be supplied to the combustion chamber, preferably without intermediate compression. Thus, employing pressure electrolysis unit leads to a reduction of the process costs for generation of electricity by a gas turbine process. Since there is no need for providing a compressor between oxygen storage and combustion chamber, this substantially helps in reducing costs and improving the efficiency.

By storing the hydrogen flow and/or oxygen flow and/or energy-carrier flow generated in the reactor unit in appropriate storage units, said flows can be used as and when required and/or as raw material or energy source outside the energy-carrier production installation according to the invention. By storing the generated energy-carrier flow it is possible to utilize larger or smaller quantities of the same for generating electricity in the energy-carrier production installation as and when required, so as to be able to provide steady quantities of electricity, thus ensuring optimal use of renewable energies for the generation of electricity.

Furthermore, it is also possible to store carbon dioxide from the flue gas and/or or an external carbon dioxide flow in a storage unit and to supply the same to a reactor unit as required. In order to be stored, the carbon dioxide flow can be compressed, preferably liquidized. By burning the energy-carrier flow using pure oxygen it is possible to produce a an exhaust gas containing pure carbon dioxide and water vapor, thus making it possible to produce a highly pure carbon dioxide by separating the water vapor.

A condensate stream, separated from the reactor unit and/or the flue gas during cooling of the same and/or a coolant flow from the reactor unit can preferably be supplied to the combustion chamber in order to provide a temperature control of the combustion reactions in the combustion chamber. By introducing the condensate flow from the reactor unit, for instance a distillate flow from a methanol plant, into the combustion chamber, the temperature of the flue-gas is lowered thus allowing controlling the temperature of the flue-gas. Moreover, the condensate flow from the reactor unit and/or the flue-gas can have higher hydrocarbons, which are converted or burned in the combustion chamber. Thus, purification of water can be dispensed with, simplifying the process and thus improving the profitability. Alternatively or in addition it can be provided for a condensate flow from the reactor unit and/or a condensate flow separated from flue-gas to be used as feed water of the electrolysis unit.

In order to utilize the waste heat, it can be provided for the heat of the reaction which is released during generation of the energy-carrier flow in the reactor unit to be exported from the reactor unit. It is advantageous to use the heat of the reaction for preheating or post-heating of above mentioned source streams. A distant heating system is also possible. For instance, the reactions involved in the catalytic conversion of carbon dioxide into methanol or methane are exothermic reactions, possibly using reaction heat. In addition, waste heat form the electrolysis process is available, which for instance can be fed into a distant heating system.

The energy-carrier production installation according to the invention comprises at least one electrolysis unit, at least one reactor unit and at least one combustion chamber and is designed for the above described process. In addition, at least one gas turbine and/or at least one steam turbine can be provided for realizing the gas or steam turbine process. And lastly it is possible to provide storage units for storing the hydrogen and/or oxygen generated in the electrolysis unit and/or for the energy-carrier generated in the reactor unit and/or for carbon dioxide separated from the flue-gas. Heat exchanger, compressor and corresponding conduits are also components of the energy-carrier production installation, with the above list not being exhaustive.

There are a number of possibilities for implementing and further improving the method and energy-carrier production installation according to the invention which can be gathered from the dependent claims and the following detailed description of a preferred embodiment of the invention with reference to the drawing.

BRIEF DESCRIPTION OF THE DRAWING

The only FIGURE of the drawing shows a diagram of a method for carbon-dioxide-neutral compensation for generation peaks and generation troughs in the generation of electrical energy from regenerative energy sources such as wind energy and/or energy from photovoltaic plants.

DETAILED DESCRIPTION OF THE INVENTION

For implementing the method, an energy-carrier production installation 1 is provided.

The installation 1 comprises one electrolysis unit 2, one reactor unit 3 and one combustion chamber 4. The electrolysis unit 2 uses electrical power 5 which is not generated in a steady manner or which is available in fluctuating quantities, for instance electrical power generated through wind power plants or photovoltaic plants, in order to produce a hydrogen flow 6 and an oxygen flow 7. Hydrogen and oxygen are preferably produced by pressure electrolysis, which compared to atmospheric electrolysis is advantageous, in that the product gases hydrogen and oxygen are delivered with a pressure of preferably 30 to 80 bar, in particular 60 bar. Alternatively or in addition to electricity 5 from regenerative energy sources it can be provided to use electricity generated from other energy sources, in particular fossil energy sources (cost-effective) for the electrolysis of water. Preferably, the electricity for the electrolysis is generated on-site in the energy-carrier production installation 1. In this case, the energy-carrier production installation 1 can comprise a wind power plant and/or photovoltaic plant and/or for instance a gas turbine. In principle, it is also possible to draw the electricity required for the electrolysis of water from a public electricity network, which will be explained in the following.

In a next step of said method, the compressed hydrogen flow 6, which, can be combined as required with an additional hydrogen flow 9 from a biomass plant 10 is supplied to a buffer tank functioning as storage unit 11 and together with a carbon dioxide flow 12 is subsequently converted into methanol as energy-carrier in the reactor unit 3 by catalytic conversion. A methanol stream in form of an energy-carrier flow containing hydrocarbon 13 is discharged from the reactor unit 3, which is stored temporarily in methanol tanks, functioning as additional storage units 14.

Subsequently, the thus produced energy-carrier flow 13 can be burned partially and as required in the combustion chamber 4. For this purpose the energy-carrier flow 13 is fed into the combustion chamber 4 via a pump 14*a*.

The thermal energy of the flue-gas flow 15 formed during combustion is used for the generation of electrical energy in an associated gas- and steam turbine process, wherein the flue-gas flow 15 can be utilized as carbon source for the generation of the energy-carrier flow 13 which contains hydrocarbon. For this purpose, a carbon dioxide flow 17 is separated from the flue-gas flow. Here, the invention provides for the carbon dioxide flow 17 to be stored temporarily in another storage unit 18 and to be fed into the reactor unit 3 as required. Preferably, the carbon dioxide flow 17 is liquefied with help of a compressor 19 and stored under pressure, so that the carbon dioxide can be supplied to the methanol process under pressure in order to be converted together with the hydrogen flow 6 from the electrolysis unit 2 into methanol. In principle, it is also possible alternatively or in addition to feed a carbon dioxide stream 20 from an external carbon dioxide source into the reactor unit 3. In this case, surplus methanol can be generated, which is discharged as energy-carrier flow 21 and available for use outside the installation 1.

The oxygen flow 7 from the electrolysis unit 2 is compressed by means of a compressor 22, fed into an oxygen storage unit 23 and stored there temporarily. Subsequently an oxygen flow 24 from another storage unit 23 is fed together with the energy-carrier flow 13 into the combustion chamber 4, in this case methanol, and is converted stoichiometrically into water and carbon dioxide. By using pure oxygen for the combustion it is possible to obtain almost pure carbon dioxide as flue-gas flow 15.

Since combustion with pure oxygen produces high combustion temperatures, it is provided for the installation 1 as shown in the FIGURE, to induce, preferably to inject into the combustion chamber 4 a heated water stream 25, preferably a coolant or a condensate charged with higher hydrocarbons from the methanol plant thus allowing for easy control and monitoring of the combustion process.

The flue gas 15 leaving the combustion chamber 4 is cooled via two heat exchangers 26, 27 and decompressed via a gas turbine 28. After decompression, the flue gas 15 is utilized for generating a flow of saturated steam 29 in another heat exchanger 30 before finally being cooled in a separator 31 by using an external coolant flow 32 in such a manner, that carbon dioxide is discharged as gas phase, forming the carbon dioxide flow 17.

A condensate flow 33 which is discharged from the separator 31 can be fed into the water tank 34 of the electrolysis unit 2. Alternatively or in addition, a condensate flow 35 from the reactor unit 3 can be fed into the water tank 34. As an alternative or in addition it is also possible to provide a pure water flow 36 as water supply for the electrolysis unit 2.

The saturated steam flow 29 is overheated in the heat exchanger 27 and in a first step 37 fed into a gas turbine. Preferably, the gas turbine works with intermediate superheating, with the intermediate superheating taking place in the heat exchanger 26. Accordingly, a second step 38 is provided for the steam turbine. Generation of electrical power 16 is carried out in the conventional manner by means of a generator unit 39. The thus generated electric power 16 can also be used for the electrolysis of water in the electrolysis unit 2 and/or can be fed into an electrical power supply system 40 as shown in the diagram, in order to compensate a lower current level in an electrical power supply system as a result of a generation trough. In case of generation peaks, as already mentioned, it is possible to draw electricity from the same electrical power supply system 40 in order to reduce the electric power available in the power supply system, wherein electricity drawn from the electrical power supply system 40 can be utilized for the electrolysis of water in the electrolysis unit 2.

Further, as can be seen in the drawing of the installation 1, treatment of waste water can be dispensed with in the installation 1, if the condensate flow 33 from the separator 31 and the condensate flow 35 from the reactor unit 3 are fed into the electrolysis unit 2. As explained above, waste water from the separator 31 and/or the reactor unit 3 can also be converted in the combustion chamber 4, which again makes treatment of waste water superfluous.

Besides the energy-carrier generated in the reactor unit 3 other gaseous or liquid fuels can be also be fed into the combustion chamber 4, so that in principle the installation 1 can also be used for producing the energy carrier meant for external use only. In this case, the entire energy-carrier flow 13, generated in the reactor unit 3 is stored in the storage units 14 and discharged from the installation 1 as energy-carrier flow 21. So for instance, it is possible to burn a natural gas flow 41 as carbon source in the combustion chamber 4 along with the oxygen 24, wherein the carbon dioxide, which is released, is fed into the reactor unit 3. At the same time, electric power is generated, which can be used at least partially for the electrolysis of water.

Thus, the installation 1 as illustrated in the single FIGURE, facilitates a carbon dioxide-neutral operation in power plant operations. That is, when the energy-carrier flow 13 generated in the reactor unit 3 is burned at least partially, as well as in production operations, (i.e., when the entire energy-carrier which has been generated is intended for external use only), no carbon dioxide is released into the atmosphere. Likewise, no nitrogen oxides or sulphur oxides are released into the environment. Thus, it is possible to compensate fluctuations caused in the supply of electricity 5 from regenerative energy sources to the installation 1 by conversion into electricity of the energy-carrier flow 13 or by conversion into electricity of an external energy-carrier (fossil), for instance by supplying natural gas, ensuring a steady supply of electricity to the electrical power supply system 40. Depending on the volume of the storage units 11, 14, 18, 23 it is possible to compensate fluctuating supplies of renewable energy over long periods of time in form of a steady current output and, as required, larger or smaller quantities of electricity can be made available at a short notice. If required, said installation 1 can also function as carbon dioxide sink, with carbon dioxide from external sources being fed into the installation 1 as carbon dioxide flow 20.

Furthermore, the waste heat from the electrolysis and waste heat form the gas and turbine process can be fed into a district heating network or used directly for pre-heating material flows in the installation 1.

In particular, by using pure oxygen for the combustion it is possible to obtain a very pure carbon dioxide flow, without it being necessary for the gas phase from the separator 31 to be subjected to a chemical and/or physical treatment, such as carbon dioxide wash.

Furthermore, it can be provided for the reaction heat from the reactions (exothermal) taking place inside the reactor unit 3 during the generation of the energy-carrier flow 13 containing hydrocarbon to be utilized for the evaporation of a water flow 42, wherein the thus formed water vapor 43 can be supplied to an additional combustion chamber 44. In the additional combustion chamber 4, hydrogen 6 is burned with oxygen 7 from the electrolysis unit, causing overheating of the water vapor 43 and thus generating superheated vapor 45. Said vapor can be used in a steam turbine process for the generation of electrical energy, which has not been show in detail.

It is understood that the above described features are only characterizing a single preferred embodiment of the energy-carrier production installation 1 and that it is not compulsory for the same to be provided in the combination as shown in the drawing. Different combinations of the described features are also possible, even though they have not been described in detail.

Below some of the possible operating conditions of the installation 1 are described:

Operating the installation at steady supply: 7220 kW of electrical energy are fed into the electrolysis unit, generating 1680 $Nm^3/h$ H2 and 840 $Nm^3/h$ O2. The MeOH quantity (methanol quantity) which is generated is 0.8 t/h. Said quantity is fed into the combustion chamber along with 840 $Nm^3/h$ O2, thus generating 4200 kW. The CCPP process yields 560 $Nm^3/h$ of CO2.

In this type of operation, liquids and gases stored in the storage unit 11, 14, 18, 23 are neither extracted nor added. The level of efficiency in relation to the amount of electricity supplied/fed into the grid is approx. 60%.

Operation with electricity surplus: For instance, 14440 kW are fed into the electrolysis, generating 3360 $Nm^3/h$ H2 and 1680 $Nm^3/h$ O2. The MeOH quantity (methanol quantity) which is produced is 1.6 t/h. From this quantity 0.8 t/h is fed into the combustion chamber 4 together with 840 $Nm^3/h$ O2, generating 4200 kW. The CCPP-process yields 560 $Nm^3/h$ CO2.

In this operation, the methanol storage unit 14 and the oxygen storage unit 23 are filled up and the carbon dioxide storage 18 is emptied.

The level of efficiency in relation to the amount of electricity supplied/fed into the grid is approx. 30%. In addition 0.8 t MeOH/h are produced.

Operation with shortage of electricity: For instance, 3610 kW are fed into the electrolysis, generating 840 Nm$^3$/h H2 and 420 Nm$^3$/h O2. The MeOH quantity (methanol quantity) which is thus generated is 1.6 t/h. From this quantity 0.8 t/h is fed into the combustion chamber 4 along with 840 Nm$^3$/h O2, generating 4200 kW. The CCPP process yields 560 Nm$^3$/h CO2.

In this operation, the methanol storage unit 14 and the oxygen storage unit 23 are emptied and the carbon dioxide storage 18 is recharged.

The level of efficiency achieved—in relation to the amount of electricity supplied/fed into the grid—is approx. 116%, with 0.4 MeOH/h being used.

To produce electricity and methanol at the same time, a natural gas operation of the installation 1 can be provided. Thus no methanol is burned.

Operation by burning natural gas: 7220 kW are fed into the electrolysis, generating 1680 Nm$^3$/h H2 and 840 Nm$^3$/h O2. The MeOH quantity (methanol quantity) which is generated is 0.8 t/h said quantity is stored. With 840 Nm$^3$/h O2 and 3.58 Gcal/h of natural gas (calculated as CH4=4160 kW chemical) 3950 kW are generated. The CCPP process yields 420 Nm$^3$/h CO2.

In this operation, approx. 140 Kg/h of CO2 are taken from the carbon dioxide storage 18, the oxygen storage is neither charged nor emptied and the methanol storage units 14 are supplied 0.8 t/h of MeOH.

The invention claimed is:

1. A method for carbon-dioxide-neutral compensation for current level fluctuations in an electrical power supply as a result of generation peaks and generation troughs in the generation of electrical energy, the method comprising:
    during a generation peak:
    using electrical energy produced from a regenerative energy source in an electrolysis unit of an energy-carrier production installation for hydrogen generation by electrolysis of an aqueous medium; and
    supplying a hydrogen flow generated in the electrolysis unit to a reactor unit of the energy-carrier production installation that catalytically generates an energy-carrier flow containing a hydrocarbon; and
    during a generation trough:
    at least partially burning the energy-carrier flow containing the hydrocarbon produced by the reactor unit in a combustion chamber of the energy-carrier production installation;
    using thermal energy of a flue-gas flow formed by the combustion chamber to generate electrical energy in at least one of a gas turbine process and steam turbine process in situ at the energy-carrier production installation;
    feeding the electrical energy generated by the at least one of a gas turbine and steam turbine into the electrical power supply; and
    supplying at least part of the flue-gas flow to the reactor unit as a carbon source for generation of the energy-carrier flow containing hydrocarbon,
        wherein only the flue-gas formed in the combustion chamber of the energy-carrier production installation is supplied to the reactor unit as said carbon source for generation of the energy-carrier flow containing hydrocarbon, so that the production of an energy-carrier as well as the use of the energy-carrier to generate electrical energy by combustion of the energy-carrier is realized at the energy-carrier production installation in a manner that provides a carbon-dioxide-neutral compensation for current level fluctuations as a result of generation peaks and generation troughs.

2. The method of claim 1, further comprising supplying an oxygen flow generated in the electrolysis unit to the combustion chamber.

3. The method of claim 2, wherein:
    the electrolysis unit is a pressure-electrolysis unit; and
    the method further comprises generating by the pressure-electrolysis unit the hydrogen flow and the oxygen flow, hydrogen of the hydrogen flow or oxygen of the oxygen flow having a pressure of 10 to 200 bar.

4. The method of claim 2, wherein:
    the electrolysis unit is a pressure-electrolysis unit; and
    the method further comprises generating by the pressure-electrolysis unit the hydrogen flow and the oxygen flow, hydrogen of the hydrogen flow or oxygen of the oxygen flow having a pressure of 30 to 100 bar.

5. The method of claim 2, wherein:
    the electrolysis unit is a pressure-electrolysis unit; and
    the method further comprises generating by the pressure-electrolysis unit the hydrogen flow and the oxygen flow, hydrogen of the hydrogen flow or oxygen of the oxygen flow having a pressure of 60 to 80 bar.

6. The method of claim 2, further comprising:
    storing the oxygen of the oxygen flow generated by the electrolysis unit in the storage unit at a storage pressure of at least 30 bar; and
    extracting the oxygen from the storage unit and supplying the oxygen to the combustion chamber at the storage pressure.

7. The method of claim 1, further comprising:
    storing the oxygen of an oxygen flow generated by the electrolysis unit in the storage unit at a storage pressure of at least 60 bar; and
    extracting the oxygen from the storage unit and supplying the oxygen to the combustion chamber at the storage pressure.

8. The method of claim 6, wherein supplying the oxygen to the combustion chamber at said storage pressure comprises supplying the oxygen to the combustion chamber without intermediate compression.

9. The method of claim 1, further comprising supplying a coolant or a condensate stream to the combustion chamber, wherein the coolant or the condensate stream is one of: supplied from the reactor unit, and separated from the flue-gas flow.

10. The method of claim 1, further comprising supplying a coolant or a condensate stream to the electrolysis unit, wherein the coolant or the condensate stream is one of: supplied from the reactor unit, and a separated from the flue-gas flow.

11. The method of claim 1, further comprising extracting the reaction heat released during generation of the energy-carrier flow in the reactor unit from the reactor unit.

12. The method of claim 1, wherein the reactor unit generates the energy-carrier flow containing the hydrocarbon using at least one of: hydrogen and carbon dioxide, and carbon monoxide.

13. The method of claim 1, wherein an additional reactor unit generates the energy-carrier flow containing the hydrocarbon using methanol or methane.

14. The method of claim 1, wherein part of the energy generated in the at least one of the gas turbine process and the steam turbine process is reserved for internal use by the energy-carrier production installation.

15. The method of claim 14, wherein the reserved part of the energy generated is used for at least one of the compaction of material flows and electrolysis of water to produce the hydrogen flow in the electrolysis unit.

* * * * *